United States Patent
Giorgetti

(10) Patent No.: US 10,272,059 B2
(45) Date of Patent: Apr. 30, 2019

(54) AMINOACID-BASED COMPOSITION FOR FIBROELASTIN RECOVERY IN DERMAL CONNECTIVE TISSUES

(71) Applicant: Professional Dietetics S.P.A., Milan (IT)

(72) Inventor: Paolo Giorgetti, Milan (IT)

(73) Assignee: Professional Dietetics S.P.A., Milan (IT)

( * ) Notice: Subject to any disclaimer, the term of this patent is extended or adjusted under 35 U.S.C. 154(b) by 0 days.

(21) Appl. No.: 15/531,805

(22) PCT Filed: Dec. 3, 2015

(86) PCT No.: PCT/IB2015/059330
§ 371 (c)(1),
(2) Date: May 31, 2017

(87) PCT Pub. No.: WO2016/088078
PCT Pub. Date: Jun. 9, 2016

(65) Prior Publication Data
US 2017/0326089 A1 Nov. 16, 2017

(30) Foreign Application Priority Data

Dec. 4, 2014 (IT) .............. MI2014A2084

(51) Int. Cl.
| | |
|---|---|
| *A61K 31/198* | (2006.01) |
| *A61K 31/401* | (2006.01) |
| *A61K 31/728* | (2006.01) |
| *A61K 8/44* | (2006.01) |
| *A61K 8/49* | (2006.01) |
| *A61K 8/73* | (2006.01) |
| *A61K 9/00* | (2006.01) |
| *A61Q 19/08* | (2006.01) |
| *A61Q 11/00* | (2006.01) |
| *A61K 8/02* | (2006.01) |
| *A61K 9/06* | (2006.01) |

(52) U.S. Cl.
CPC ............ *A61K 31/198* (2013.01); *A61K 8/022* (2013.01); *A61K 8/44* (2013.01); *A61K 8/4913* (2013.01); *A61K 8/735* (2013.01); *A61K 9/0014* (2013.01); *A61K 9/0019* (2013.01); *A61K 9/0053* (2013.01); *A61K 9/0095* (2013.01); *A61K 9/06* (2013.01); *A61K 31/401* (2013.01); *A61K 31/728* (2013.01); *A61Q 11/00* (2013.01); *A61Q 19/08* (2013.01); *A61K 2800/5922* (2013.01); *A61K 2800/91* (2013.01)

(58) Field of Classification Search
CPC .. A61K 31/198; A61K 31/401; A61K 31/728; A61K 8/44; A61K 9/0053; A61K 8/735; A61K 8/4913; A61K 2800/5922; A61Q 19/08
USPC .............................. 514/54; 435/106
See application file for complete search history.

(56) References Cited

U.S. PATENT DOCUMENTS

| | | | |
|---|---|---|---|
| 2008/0102107 A1 | 5/2008 | Lewellyn et al. | |
| 2011/0160137 A1* | 6/2011 | Kim ............. | A61K 8/365 |
| | | | 514/17.2 |
| 2012/0121534 A1* | 5/2012 | Thorel ........... | A61K 8/675 |
| | | | 424/78.37 |

FOREIGN PATENT DOCUMENTS

| | | |
|---|---|---|
| EP | 2033689 A1 | 3/2009 |
| FR | 2849383 A1 | 7/2004 |
| WO | 2007048522 A1 | 5/2007 |
| WO | 2011064297 A1 | 6/2011 |

OTHER PUBLICATIONS

Search Report and Written Opinion of PCT/IB2015/059330 dated Mar. 11, 2016.

* cited by examiner

*Primary Examiner* — Yih-Horng Shiao
(74) *Attorney, Agent, or Firm* — Silvia Salvadori, P.C.; Silvia Salvadori

(57) ABSTRACT

The present invention relates to compositions containing, as active ingredient, a mixture of amino acids able to stimulate the biosynthesis of elastin and collagen.

12 Claims, 2 Drawing Sheets

AMINOACID-BASED COMPOSITION FOR FIBROELASTIN RECOVERY IN DERMAL CONNECTIVE TISSUES

This application is a U.S. national stage of PCT/IB2015/059330 filed on 3 Dec. 2015, which claims priority to and the benefit of Italian Application No. MI2014A002084 filed on 4 Dec. 2014, the contents of which are incorporated herein by reference in their entireties.

The present invention relates to compositions containing, as active ingredient, a mixture of amino acids able to stimulate the biosynthesis of elastin and collagen.

BACKGROUND OF THE INVENTION

The dermis is the median district of the skin which performs supporting and trophic functions and confers strength, elasticity, turgidity and metabolic viability on the skin as a whole. The dermis contains cells called fibroblasts, i.e. specialised cells of mesenchymal origin, which continuously regenerate the interstitial matrix mainly consisting of glycosaminoglycans (GAGS) and proteoglycans (PGs), hydrophilic substances of a glycoside and glycopeptide nature respectively. Said macromolecules retain large amounts of water, constituting a hydrophilic network in gel form in which all the fibrous proteins that give the skin its strength and tone are immersed.

The fibroblasts are also responsible for synthesis of elastin, a protein with elastic properties that gives the skin and mucous membranes the fundamental property of adapting to the morphological and mechanical changes they undergo.

Elastin is capable of stretching up to 7 times its own length and returning to its dimensional modulus without significant molecular alterations, and can theoretically repeat this stretching an unlimited number of times.

The conditions known as skin aging and photoaging represent the objective dermatological manifestations of highly complex biochemical phenomena involving the cells, the superficial tissue structures and, above all, the deep tissue structures.

Photoaging causes the appearance of wrinkles of varying numbers and depths on the skin surface, especially where it is exposed to light (face, neckline and torso), elastosis and more or less diffuse pigmented spots, epidermal thickening and freckles. The elastic component of the skin, represented by the network of elastin fibres located in the distal part of the dermal tissue (reticular dermis), undergoes significant alterations as a result of the photoaging phenomena described above, causing a significant loss of the total elastic capacity of the skin. At macroscopic level, said phenomena reduce the ability of the connective tissue of the skin to adapt to mechanical stretching, leading to tissue sagging and elastosis.

The gene encoding the protein tropoelastin (ELN-gene), which is the precursor of elastin, is unique; there are not several genes (superfamily) encoding different forms of elastin as is the case with collagen [1]. Said gene encodes different forms of tropoelastin (thus there is probably a different tropoelastin encoding process for healthy and newly-formed tissues, for example in response to physical damage such as burning or photoaging); it already begins to be expressed at the foetal stage, remaining active for the first 5 years of life and then slowing drastically, until its activity stops [1,2]. In other words, the elastic component of connective tissue, and in particular of the dermis, mucous membranes, cartilage tissue, tunica intima, pulmonary and valvular/myocardial connective tissue, already ceases to be synthesised in the early years of life. Said component consequently represents the body's "elasticity supply" and is never replenished during its lifetime, except in the event of serious tissue damage, such as burns and severe photoaging. In these cases there is over-expression of the LOX (lysine oxidase) genes, which encode 5 different enzymes that catalyse oxidation of the lysine residues in the tropoelastin precursor molecules, a necessary step for the synthesis of functional elastin and its subsequent incorporation in the microfibrils adhering to the cell surface [3,4]. In particular, said enzyme-dependent process consists of lysine oxidation and simultaneous formation of a Schiff base between the amino group of L-LYS and an aldose, to give rise to a crosslinked intramolecular bond [5,6]. Elastin is the only connective tissue protein that is substantially not replaced, and remains the same for over 70 years (mean half-life 74 years).

In the case of collagen, type IV collagen plays a key role in the process of structuring the basal dermoepidermal membrane and the supramolecular organisation of extracellular matrix (ECM), with special reference to cell orientation in the matrix. A collagen IV deficiency is closely correlated with loss of the trophism and elastic power of human skin, especially in the skin degeneration phenomena typical of skin aging and photoaging [7,8].

Specific combinations of amino acids and oligopeptides, if suitably carried and applied topically or orally, are known to promote the gene expression that gives rise to new protein synthesis in the dermoepidermal connective tissue, mucous membranes and joint cartilage, especially the synthesis of collagen and tropoelastin [9,10,11,12].

One of the main phenomena involved in the progressive decline of the elastic function of the dermoepidermal tissues in skin aging and photoaging is represented by progressive loss of biosynthesis activity by the fibroblasts, the cells responsible for regeneration of the collagen and elastin proteins and of the dermal extracellular matrix (ECM). As a result of this phenomenon, in the event of insufficient or low synthesis of new structural dermal proteins and hydrophilic extracellular matrix, their degradation by specific catabolic enzymes called elastase, metalloproteinase, collagenase and gelatinase increases [13,14,15]. Said enzymes, which are hyperexpressed and synthesised in the mitochondria of aging fibroblasts and the macrophages, shift the "synthesis-demolition" balance towards demolition, leading to a slow but progressive deterioration of the tissue, which thus becomes less compact, less elastic and less hydrated (deficiency of GAGs, PGs and fibroelastin component). To inhibit or at least limit said phenomenon, which is partly physiological but exacerbated by various environmental and genetic causes, it is necessary to promote the expression of genes that induce the synthesis of structural proteins in the fibroblasts (tropoelastin and collagen) in all areas wherein the latter are present, and at the same time reduce the, expression of genes responsible for encoding metalloproteinases, particularly those specialising in the degradation of collagen and elastin (collagenase and elastase).

In view of the increased catabolic activities mediated by gene hyperexpression of matrix-degrading enzymes, especially collagenase and elastase, topical or injective application, directly into the dennoepidermal tissue, mucous membranes or joints, of substances with proven activity inhibiting the expression of said enzymes, is particularly strategic. In particular, N-acetylcysteine, the N-acetylated form of the sulphurated amino acid L-cysteine, exhibits an evident action inhibiting the expression of metalloelastases induced by photo-irradiation [16]. Its simultaneous introduction into polyaminoacid compositions that perform an elastogenic and collagenic activity is advantageously usable to promote recovery and maintenance of the elastin and collagen content of the connective tissue.

Hyaluronic acid (HA) is the main GAG present in the amorphous interstitial matrix of connective tissue.

GAGs (glycosaminoglycans) are polysaccharide molecules consisting of repeating mono- or disaccharide units; hyaluronic acid is a polyglucodimer consisting of N-acetyl glucosamine and glucuronic acid. HA is the only GAG whose molecule does not include sulphate groups, and the only one with an unbranched linear structure. The other GAGs present in the amorphous matrix of connective tissue, and components of other connective tissue structures such as tendons and cartilage, are chondroitin sulphate, keratan sulphate, heparan sulphate, dermatan sulphate and heparin. HA performs crucial hydrating functions in ECM, promoting cell mobility, exchange of nutrients and soluble protein factors, and modulating the biochemical phenomena of regeneration and organisation of the fibro-connective tissue matrix.

Mixtures of amino acids for injectable, topical or oral use are disclosed in EP 2 033 689, WO 2007/048522 and WO 2011/064297. However, none of the compositions disclosed contains a mixture of glycine, L-proline, L-alanine, L-valine, L-leucine and L-lysine hydrochloride in suitable ratios, able to stimulate the synthesis of both collagen and elastin.

DESCRIPTION OF THE INVENTION

Figure 1:
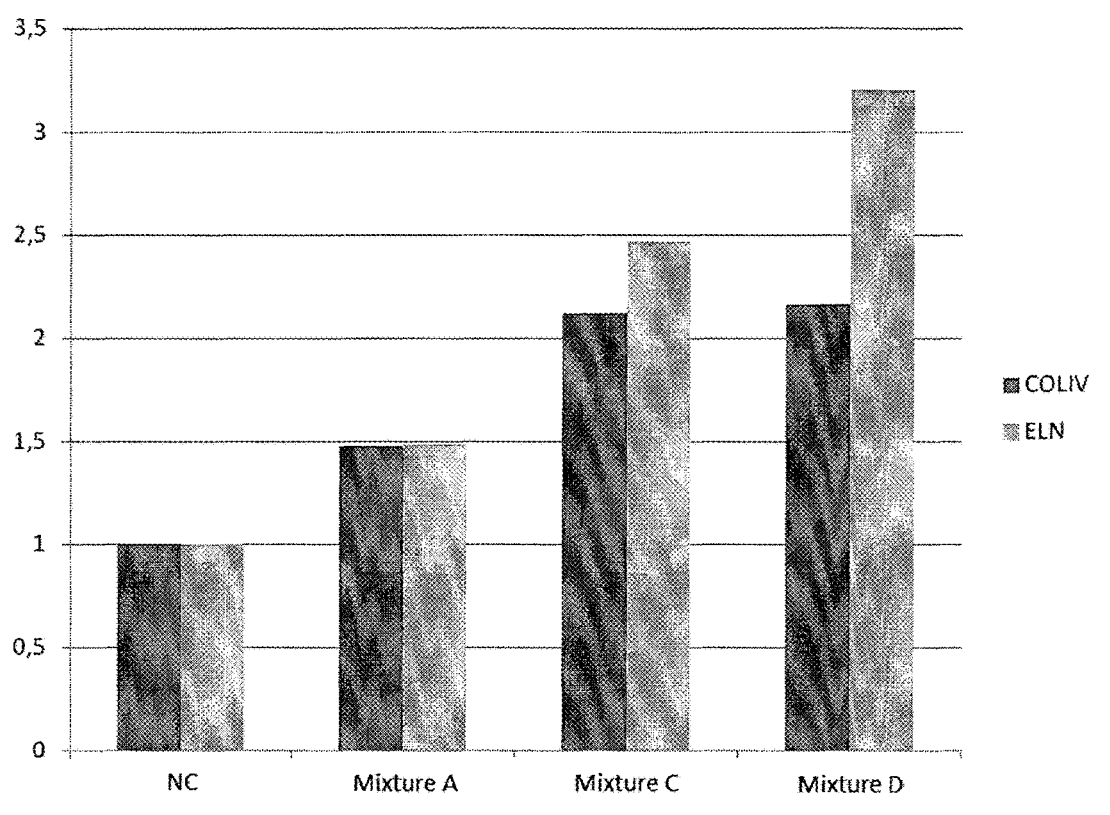
FIG. 1 shows the results of the post-translational study.

The invention relates to compositions containing a mixture of amino acids that selectively trigger the expression of genes encoding tropoelastin (ELN), lysine oxidase (LOXL-1) and Type IV collagen (COL4A1) and inhibit the expression of genes encoding metalloelastases.

The mixture of amino acids according to the invention consists of glycine, L-proline, L-alanine, L-valine, L-leucine and L-lysine hydrochloride in the following weight ratios:
Glycine 1;
L-proline: 0.7-0.8;
L-alanine: 0.47-0.76;
L-valine: 0.35-0.56;
L-leucine: 0.13-0.27;
L-lysine hydrochloride: 0.10-0.12.
L-cysteine or N-acetyl-L-cysteine may also be present in percentages by weight ranging between 1 and 20% of the total amino acid mixture.

The preferred weight ratios are:
Glycine 1;
L-proline: 0.75;
L-alanine: 0.48-0.51;
L-valine: 0.35-0.37;
L-leucine: 0.13-0.15;
L-lysine hydrochloride: 0.10-0.11, or:
Glycine 1;
L-proline: 0.75;
L-alanine: 0.75-0.76;
L-valine: 0.54-0.56;
L-leucine: 0.13-0.14;
L-Lysine hydrochloride: 0.10-0.11, or
Glycine 1;
L-proline: 0.75;
L-alanine: 0.75-0.76;
L-valine: 0.54-0.56;
L-leucine: 0.13-0.14;
L-Lysine hydrochloride: 0.10-0.11, or
Glycine 1;
L-proline: 0.75;
L-alanine: 0.49-0.51;
L-valine: 0.35-0.36;
L-leucine: 0.26-0.27;
L-lysine hydrochloride: 0.10-0.11.

Said compositions may be in a form suitable for oral administration, such as solutions, granules, dispersible powder, tablets or capsules.

The compositions according to the invention may also contain hyaluronic acid or salts thereof, in particular sodium hyaluronate, with an average molecular weight ranging between 500,000 and 3,000,000 Da, in percentages ranging between 0.01 and 3% by weight of the total composition. Said compositions containing the mixture of amino acids described above and hyaluronic acid are suitable for topical or injectable use. Examples of usable formulations include gels, ointments, emulsions, transdermal patches, sterile solutions and sterile amino-acid powders designed to be reconstituted with sterile aqueous solutions of hyaluronates.

In the case of oral formulations, the unit doses of glycine range between 100 and 1500 mg.

In the case of injectable formulations, the unit dose of glycine ranges between 10 and 50 mg, and those of hyaluronic acid or its sodium salt between 10 and 100 mg.

In the case of topical formulations, the glycine concentration can range from 0.1 to 2% mg/ml.

The compositions according to the invention are useful in the treatment of elastosis and dermoepidermal atrophy resulting from photoaging, skin disorders with a dermoatrophic and iatrogenic base [17], burns (including radiation burns), skin lesions, bedsores, dermal aplasia caused by drugs (antiretrovirals, anti-HIV drugs, corticosteroids or chemotherapy), tendon and joint lesions.

Using in vitro transcriptomics and proteomics, it has been found that the mixture of amino acids induces an increase in expression of the genes encoding tropoelastin (ELN) and Type IV collagen (COLIV) after 120 hours' incubation of human fibroblasts. Surprisingly, said effect is no longer present if even one of the amino acids is eliminated or the weight ratios are varied.

The delivery of amino acids in the form of aqueous solution gelled with hyaluronic acid in the form of sodium salt restores the dermal matrix plasticity and guarantees the retention of the amino acids in the dermoepidermal area for a sufficient time to induce the desired biological effect.

Injectable formulations can be prepared by dissolving the amino acids in the form of sterile powder in the sterile solution of hyaluronic acid sodium salt by introducing the hyaluronic acid (sodium salt) gel directly (e.g. with a dermal implant syringe) into the vial containing the powder. When completely dissolved, the resulting gel solution is injected into the dennoepidermal region.

The sterile aqueous solution of hyaluronic acid sodium salt may contain pH-correcting buffer agents (e.g. phosphate buffer) or osmolarity correctors (e.g. sodium chloride) and other technological adjuvants able to guarantee the physicochemical and tissue compatibility characteristics required for sterile injectable pharmaceutical forms. The invention is illustrated in detail in the following examples.

EXAMPLE 1

Sterile Solution of Sodium Hyaluronate

| Phase | Raw material | mg/3 ml |
| --- | --- | --- |
| A | SODIUM HYALURONATE (MW = 1,000,000 Daltons) | 30,000 |
| A | Phosphate buffer | q.s. pH = 7.2 |
| D | Sodium chloride | q.s. 250 < osm. < 300 |
| D | Water for injection | q.s. for 3 ml |

Sterile Amino-Acid Powder

| Phase | Raw material | mg/3 ml |
| --- | --- | --- |
| A | Glycine | 30.200 |
| A | L-leucine | 4.200 |
| A | L-valine | 16.800 |
| A | L-proline | 22.700 |
| A | L-alanine | 22.800 |
| A | L-lysine HCl (hydrochloride) | 3.300 |

EXAMPLE 2

Sterile Solution of Sodium Hyaluronate

| Phase | Raw material | mg/3 ml |
| --- | --- | --- |
| A | SODIUM HYALURONATE (MW = 1000,000 Daltons) | 30,000 |
| A | Phosphate buffer | q.s. pH = 7.2 |
| D | Sodium chloride | q.s. 250 < osm. < 300 |
| D | Water for injection | q.s. for 3 ml |

Sterile Amino-Acid Powder

| Phase | Raw material | mg/3 ml |
| --- | --- | --- |
| A | L-proline | 25.100 |
| A | L-lysine hydrochloride | 3.700 |
| A | L-valine | 12.300 |
| A | L-alanine | 16.800 |
| A | Glycine | 33.400 |
| A | L-leucine | 8.700 |

EXAMPLE 3

Sterile Solution of Sodium Hyaluronate

| Phase | Raw material | mg/3 ml |
| --- | --- | --- |
| A | SODIUM HYALURONATE (MW = 1,000,000 Daltons) | 30,000 |
| A | Phosphate buffer | q.s. pH = 7.2 |
| D | Sodium chloride | q.s. 250 < osm. < 300 |
| D | Water for injection | q.s. for 3 ml |

Sterile Amino-Acid Powder

| Phase | Raw material | mg/3 ml |
| --- | --- | --- |
| A | L-proline | 25.100 |
| A | L-lysine hydrochloride | 3.700 |
| A | L-valine | 12.300 |
| A | L-alanine | 16.800 |
| A | Glycine | 33.400 |
| A | L-leucine | 8.700 |
| A | N-acetylcysteine | 12.500 |

EXAMPLE 4

Topical Hydrogel Based on Amino Acids and Sodium Hyaluronate

| Phase | Raw material | g/100 g |
| --- | --- | --- |
| A | Glycerine | 3.000 |
| A | Water | q.s. 100 g |
| A | Glycine | 0.915 |
| A | L-proline | 0.688 |
| A | L-alanine | 0.691 |
| A | L-leucine | 0.127 |
| A | L-valine | 0.509 |
| A | L-lysine hydrochloride | 0.100 |
| A | N-acetylcysteine | 0.600 |
| B | Potassium sorbate | 0.200 |
| B | Sodium benzoate | 0.200 |
| B | Sodium hyaluronate (mw = 3000000 d) from *Streptococcus equi* | 1.200 |
| | | 100.00000 |

EXAMPLE 5

Sachets (Stickpack) for Oral Solution

| | mg/20 ml stickpack |
| --- | --- |
| Glycine | 1208 mg |
| L-proline | 908 mg |
| L-leucine | 168 mg |
| L-lysine HCl | 132 mg |
| L-valine | 672 mg |
| L-alanine | 912 mg |

Excipients: preservatives: sodium benzoate, potassium sorbate; acidity regulators: citric acid, sodium citrate.

Efficacy Tests

The efficacy of the mixtures of amino acids according to the invention was evaluated by comparison with control mixtures and hyaluronic acid mixtures in stimulating production of the structural ingredients of the extracellular matrix, especially neosynthesis of elastin, and facilitating a more efficient deposit of elastic fibres (elastogenesis), while at the same time maintaining collagen stimulation.

A primary culture of standardised human fibroblasts was used. The trial design was structured to evaluate the gene expression of elastin and collagen. Gene expression was evaluated by RT-qPCR at the following times: 24, 72 and 120 h. The production of said matrix proteins was evaluated by the Western Blot technique at 120 h.

A preliminary evaluation of the cytotoxicity of the amino acid and hyaluronic acid mixtures was conducted to identify the maximum concentration tested that was not cytotoxic. The concentration of 1000 µg/ml was selected on the basis of the data obtained.

Results of Transcriptional Study

This study included a negative control (NC), corresponding to untreated fibroblasts (physiological response). Mixture A, consisting only of the amino acids constituting collagen (Gly, L-Pro, L-Lys, L-Leu), did not induce significant gene expression. Conversely, the two mixtures containing six amino acids tested, C and D, consisting of the amino acids most expressed in both collagen and elastin (Gly, L-Pro, L-Lys, L-Leu, L-Ala and L-Val), induced significant modulation of the ELN (elastin) and COLIV (collagen IV) genes after 120 h.

The compositions of the mixtures tested are set out in the table below.

|  | Mixture A | Mixture C | Mixture D |
| --- | --- | --- | --- |
| Glycine | 50.0 | 33.4 | 30.2 |
| L-Proline | 37.5 | 25.1 | 22.7 |
| L-Leucine | 7.0 | 8.7 | 4.2 |
| L-lysine HCl | 5.5 | 3.7 | 3.3 |
| L-valine | — | 12.3 | 16.8 |
| L-alanine | — | 16.8 | 22.8 |

Gene Expression of Elastin (ELN) and Collagen IV (COLIV) Quantified by Comparison with the Control.

|  | NC | A | C | D |
| --- | --- | --- | --- | --- |
| ELN | 1 | 1.478 | 2.121 | 2.164 |
| COLIV | 1 | 1.484 | 2.464 | 3.197 |

FIG. 1 Shows the Results of the Post-Translational Study

As shown in the graph, mixture A induces an increase in the production of collagen only, while mixtures C and D significantly modulate the production of both elastin and collagen IV.

Relative Quantitation of the Proteins Collagen IV and Elastin Using NC as Reference.

|  | NC | A | C | D |
| --- | --- | --- | --- | --- |
| Elastin | 1 | 0.805 | 2.403 | 2.00 |
| Collagen IV | 1 | 1.685 | 2.547 | 2.278 |

Discussions

Figure 2:
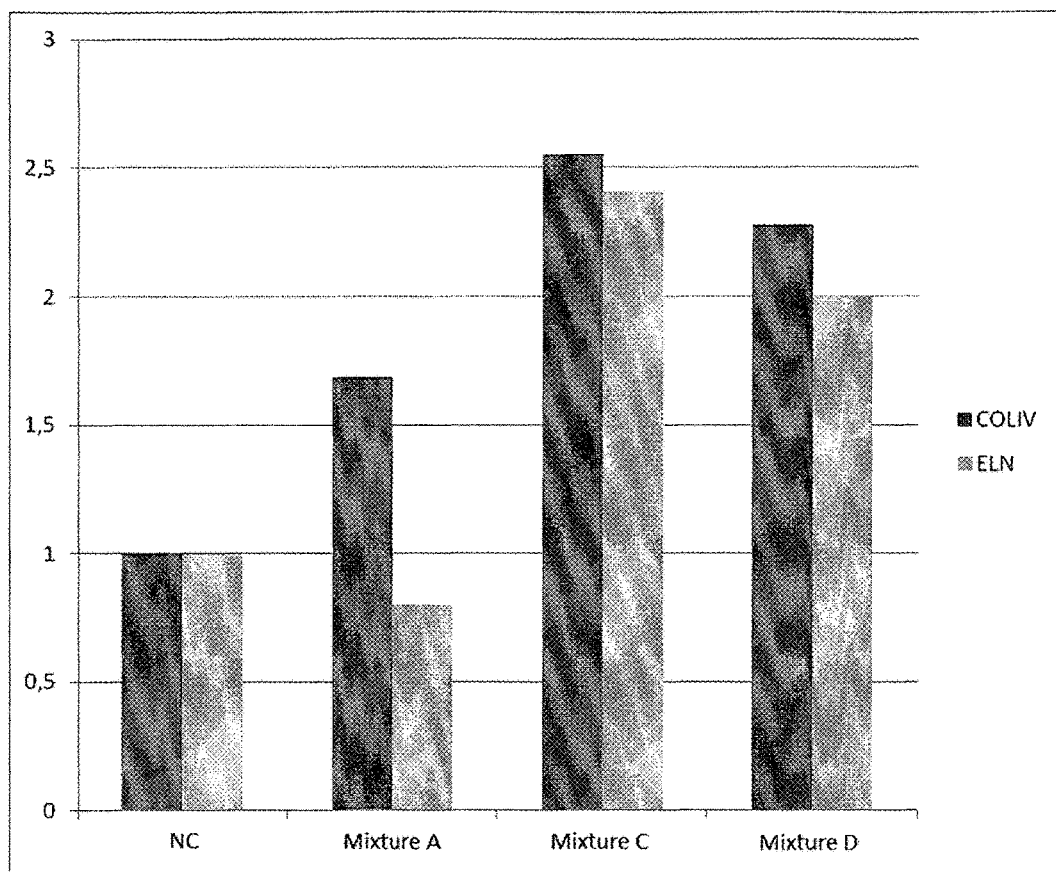
FIG. 2 shows the results of single-layer human fibroblast studies conducted on the basis of a transcriptomic approach.

The graph in FIG. 2 shows the results of single-layer human fibroblast studies conducted on the basis of a transcriptomic approach, demonstrating that only certain mixtures of amino acids, optionally combined with hyaluronic acid, can modulate the biosynthesis of the extracellular matrix proteins, and especially promote elastogenesis. Only mixtures of amino acids combined according to the ratios disclosed in this patent increase the gene and protein expression of elastin as well as boosting the stimulation of collagen (especially collagen IV).

It should be noted that the integrity and quality of the matrix is not restricted to collagen, but to the production and physiological interaction of all the structural proteins produced by the fibroblasts, especially elastin.

In fact, collagen and elastin maintain the anisotropy in the matrix, i.e. the ability of the fibres produced to propagate the tensile forces, a characteristic which is lost with age.

It has also been demonstrated that the mixtures of amino acids in question cause physiological elastin gene induction with kinetics very different from the response to UV radiation, wherein the appearance of elastin is rapid, disorderly and, by inducing elastase, actually causes degradation.

Conclusions

The results of this study demonstrate that only the mixtures according to the invention promote significant production of the two proteins. It has therefore been demonstrated that not only does an inductive mechanism exist, but the mRNA produced encodes a functional protein.

REFERENCES

1. Bashir, M M et al. (1989), J Biol Chem 264, 8887-8891.
2. Chen, Z et al., (2009), Exp Dermatol 18, 378-386.
3. Indik Z et al., (1989), Am J Med Genet 34, 81-90.
4. Cenizo V et al., (2006), Exp Dermatol 15, 574-581.
5. Maki et al., (2005), Am J Pathol 167, 927-936.
6. Noblesse et al., (2004), J Invest Dermatol 122, 621-630.
7. Abreu-Velez AM et al., N Am J Med Sci. 2012 January; 4(1):1-8.
8. Vazquez F et al., Maturitas. 1996 November; 25(3):209-15.
9. Lupo M P et al., (2007). Cosmeceutical peptides. Dermatol Ther 20, 343-349.
10. Reddy B et al., Bioactive oligopeptides in dermatology: Part I. Exp Dermatol. 2012 August; 21(8):563-8. doi: 10.1111/j.1600-0625.2012.01528.x. Epub 2012 June 4.
11. Proksch E et al., Skin Pharmacol Physiol. 2014; 27(3): 113-9.
12. Dioguardi F S, (2008) November-Cec; 26(6):636-40.
13. Fisher G J et al., J Invest Dermatol. 2001 August; 117(2):219-26.
14. Rijken F et al., J Investig Dermatol Symp Proc. 2009 August; 14(1):67-72. doi: 10.1038/jidsymp.2009.15.
15. Quan T et al., J Investig Dermatol Symp Proc. 2009 August; 14(1):20-4. doi: 10.1038/jidsymp.2009.8.
16. Chung J H et al., J Invest Dermatol. 2002 August; 119(2):507-12.
17. Schoepe S et al., Exp Dermatol. 2006 June; 15(6):406-20.

The invention claimed is:

1. Compositions containing, as active ingredient, amino acids consisting of glycine, L-proline, L-alanine, L-valine, L-leucine and L-lysine hydrochloride in the following weight ratios:
   Glycine: 1;
   L-proline: 0.7-0.8;
   L-alanine: 0.47-0.76;
   L-valine: 0.35-0.56;
   L-leucine: 0.13-0.27;
   L-lysine hydrochloride: 0.10-0.12.

2. Compositions containing, as active ingredient, amino acids consisting of glycine, L-proline, L-alanine, L-valine, L-leucine, L-lysine hydrochloride and L-cysteine or N-acetyl-L-cysteine in the following weight ratios:
   Glycine: 1;
   L-proline: 0.7-0.8;
   L-alanine: 0.47-0.76;
   L-valine: 0.35-0.56;
   L-leucine: 0.13-0.27;
   L-lysine hydrochloride: 0.10-0.12
   L-cysteine or N-acetyl-L-cysteine ranging between 1 and 20% by weight of the total amino acids.

3. The compositions as claimed in claim 1 wherein the weight ratios of the amino acids are:
   Glycine: 1;
   L-proline: 0.75;

L-alanine: 0.48-0.51;
L-valine: 0.35-0.37;
L-leucine: 0.13-0.15;
L-lysine hydrochloride: 0.10-0.11.

4. The compositions as claimed in claim 1 wherein the weight ratios of the amino acids are:
Glycine: 1;
L-proline: 0.75;
L-alanine: 0.75-0.76;
L-valine: 0.54-0.56;
L-leucine: 0.13-0.14;
L-lysine hydrochloride: 0.10-0.11.

5. The compositions as claimed in claim 1 wherein the weight ratios of the amino acids are:
Glycine: 1;
L-proline: 0.75;
L-alanine: 0.49-0.51;
L-valine: 0.35-0.36;
L-leucine: 0.26-0.27;
L-lysine hydrochloride: 0.10-0.11.

6. The compositions as claimed in claim 1, wherein the compositions are for oral use.

7. The compositions as claimed in claim 6, wherein the compositions are in the form of solutions, granules, dispersible powder, tablets or capsules.

8. Compositions containing, as active ingredient, amino acids consisting of glycine, L-proline, L-alanine, L-valine, L-leucine and L-lysine hydrochloride in the following weight ratios:
Glycine: 1;
L-proline: 0.7-0.8;
L-alanine: 0.47-0.76;
L-valine: 0.35-0.56;
L-leucine: 0.13-0.27;
L-lysine hydrochloride: 0.10-0.12 and hyaluronic acid or salts thereof, with an average molecular weight ranging between 500,000 and 3,000,000 Da, ranging between 0.01 and 3% by weight of the total composition.

9. The compositions as claimed in claim 8, wherein the compositions are for topical or injective use.

10. The compositions as claimed in claim 9, wherein the compositions are in the form of gels, ointments, emulsions, transdermal patches, sterile solutions or sterile amino-acid powders designed to be reconstituted with sterile aqueous solutions of hyaluronates.

11. A method of treating elastosis and dermoepidermal atrophy resulting from photoaging, skin disorders with a dermoatrophic and iatrogenic cause, burns, radiation burns, skin lesions, bedsores, dermal aplasia caused by drug administration or tendon and joint lesions in subjects in need thereof with the compositions according to claim 1, said method comprising;
administering to said subjects a pharmaceutical effective amount of the compositions according to claim 1.

12. The compositions as claimed in claim 8, wherein said hyaluronic acid salt is sodium hyaluronate.

\* \* \* \* \*